(12) United States Patent
Ratcliffe et al.

(10) Patent No.: US 6,799,126 B1
(45) Date of Patent: Sep. 28, 2004

(54) NONDESTRUCTIVE METHOD FOR DETECTING STRUCTURAL ANOMALIES IN COMPOSITES

(75) Inventors: Colin P. Ratcliffe, Millersville, MD (US); Roger M. Crane, Arnold, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 25 days.

(21) Appl. No.: 10/400,646

(22) Filed: Mar. 28, 2003

(51) Int. Cl.[7] .............. G06F 19/00; G01B 5/28; C21B 7/24; G01N 29/02
(52) U.S. Cl. ............. 702/56; 702/35; 702/36; 73/584; 73/598; 73/600; 73/602
(58) Field of Search ............. 702/35, 36, 39, 702/40, 56, 179; 73/579, 584, 586, 591, 596, 597, 598, 599, 600, 602

(56) References Cited

U.S. PATENT DOCUMENTS 6,301,967 B1 * 10/2001 Donskoy et al. .............. 73/579

* cited by examiner

*Primary Examiner*—John Barlow
*Assistant Examiner*—Meagan S Walling
(74) *Attorney, Agent, or Firm*—Steven W. Crabb

(57) ABSTRACT

A nondestructive inspection method for composite structures, including thick core structures, is disclosed that imparts a vibration force into the structure and analyzes the response over a range of frequencies to find possible damaged areas. The composite structure is struck to induce vibration at a series of test points and the response of the composite structure as a function of acceleration at each test point is measured. The structural anomalies in the composite structure occur at structural stiffness irregularities near anomalies and are detected with a Gapped Smoothing Method operating on the data and plotting a structural irregularity index as a function of frequency and position.

38 Claims, 7 Drawing Sheets

NONDESTRUCTIVE METHOD FOR DETECTING STRUCTURAL ANOMALIES IN COMPOSITES

STATEMENT OF GOVERNMENT INTEREST

The invention described herein may be manufactured and used by or for the Government of the United States of America for governmental purposes without payment of any royalties thereon or therefore.

BACKGROUND OF THE INVENTION

The use of composite materials to replace conventional materials such as steel, aluminum, concrete and wood is becoming more commonplace and includes large structures such as bridges, body panels in automobiles and ships, and structural supports. Often, these components are thick section composites with varying core thickness. One of the challenges presented by the expanded use of composites, is the difficultly in inspection to assess structural integrity, manufacturing quality and to identify defects.

There are more numerous flaws that can occur in composites during manufacture that can have a significant impact on service life and performance than occur in metals or concrete. Today, the primary methods of nondestructive inspection are visual and ultrasonic. The techniques used in ultrasonic inspections typically require expensive specialized equipment, a highly trained operator and take a significant amount of time to perform the inspection and analyze the results. Additionally, many of the best ultrasonic inspection techniques are not suitable for in-service inspections. Systems such as the mobile automated ultrasonic scanning system do allow for field inspections, but are slow and often only provide an assessment at a few discrete locations on the structure.

Conventional nondestructive inspection techniques have made strides in locating flaws in some composites in the plane of the material and in the thickness direction. Defects such as delamination, fiber misalignment, cracking, matrix crazing and many other characteristics may be accurately determined. However, in thick-cored structures, composites with a thickness of an inch or more, the ultrasonic inspection is either rendered useless or at most can assess damage near the surface and visual inspections are inadequate.

What is needed is a non-destructive system and method that can easily and accurately detect structural anomalies in thick section composite materials in numerous settings and applied to varied shapes.

SUMMARY OF THE INVENTION

In accordance with the invention there is provided a new nondestructive inspection method for inspecting structures. In a preferred arrangement the method includes marking a mesh of test points on the structure to be tested. Optionally, the mesh or grid of points is rectangular. A plurality of sensors are attached at various locations on the structure, preferably not on the mesh and away from structural edges. The structure is excited by imparting a vibration force in the structure twice at each test point, and the subsequent response of the structure from each force input is recorded. The frequency response function (FRF) from the vibration force excitation at each of the test points is determined and the frequency dependent Operating Deflection Shapes (ODS) are determined from the FRF at each frequency and each of the test points. The ODS is differentiated to convert the information into an Operating Curvature Shape (OCS) by applying the finite difference approximation to both the real and imaginary parts of the ODS. A gapped cubic polynomial may be fitted to the OCS of the 5 nearest linear neighbor points of the test points of the mesh with separate functions being fitted to the real and imaginary parts of the complex function where the center value of the OCS has been removed. A structural irregularity index may be calculated by calculating the difference between the experimental curvature and the values of the cubic polynomials at each frequency and each test point. The results of the structural irregularity index values across all frequencies at each of the test points are summed and the results may be plotted on a contour map.

Optionally, the ODS may be normalized to an rms value of 1 prior to differentiating to curvature.

In a preferred arrangement, the vibration force may be imparted by an impulse hammer or a mechanical shaker. In a preferred arrangement the impact force imparts vibration energy in a frequency range of one to one hundred times the fundamental frequency of the structure. Optionally, the frequency corresponds to the resonant frequencies of the structure or may be in either a selected range of frequencies or a random range of frequencies.

Optionally, the gapped cubic polynomial may be fitted to the OCS in only one direction to allow for a different view of the results. In another preferred arrangement the gapped cubic polynomial may be fitted to the OCS in two intersecting directions and the results merged.

Numerous types of sensors may be used in alternative arrangements such as fiber optic Bragg gratings, mems sensors, strain gages, or other types of acceleration or displacement transducers.

In another preferred arrangement of the invention the ODS is not normalized to an rms value of one and the rms value of the damage indices at each line is normalized to an rms value of 1.

For a better understanding of the present invention, together with other and further objects thereof, reference is made to the following description, taken in conjunction with the accompanying drawings, and its scope will be pointed out in the appended claims.

DESCRIPTION OF THE PREFERRED EMBODIMENT

Figure 1:
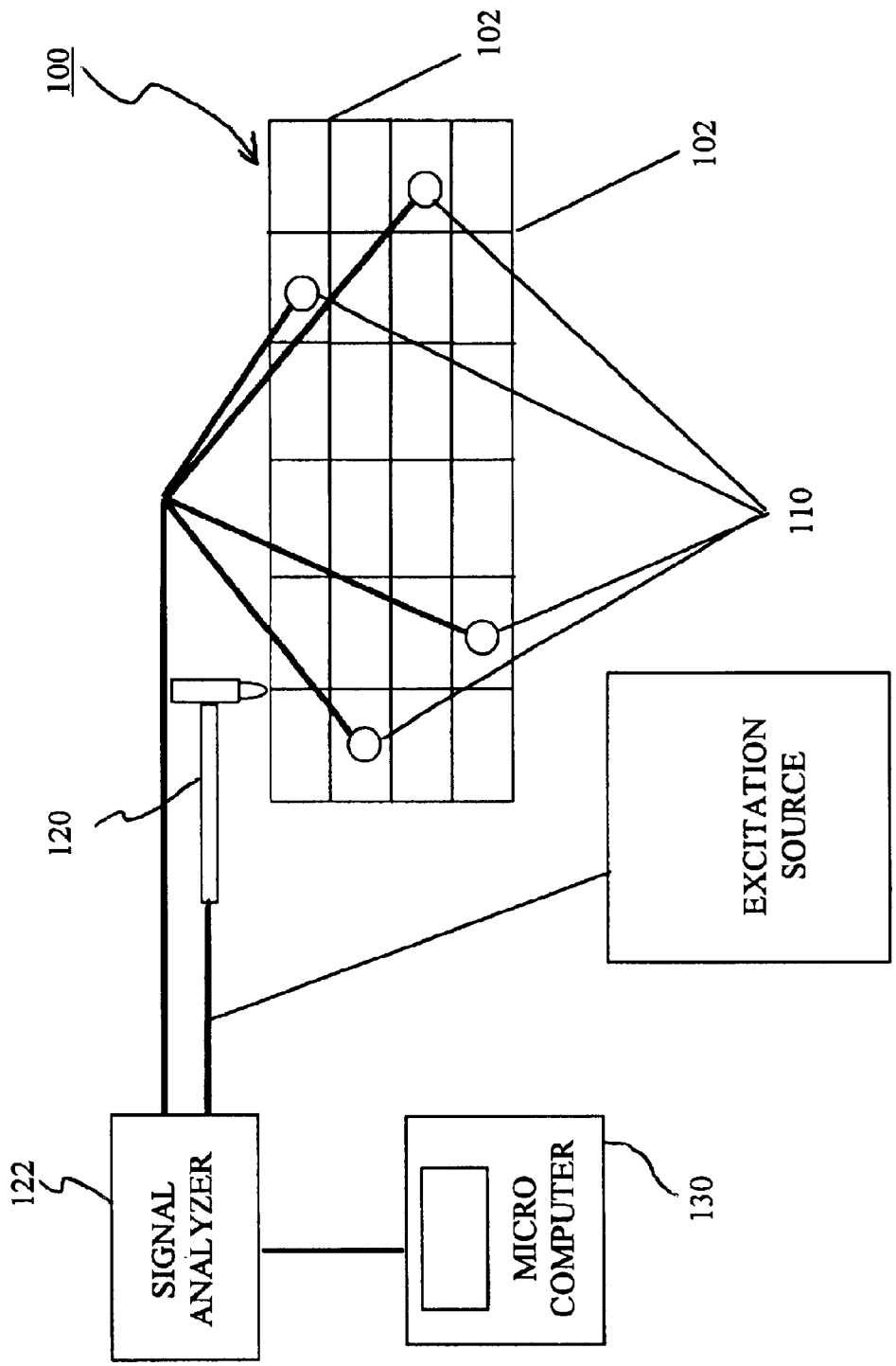
FIG. 1 illustrates a schematic diagram of an example setup to detect structural anomalies in a composite structure.

Referring to FIG. 1, an example of a test setup of the present method for testing a composite structure for anomalies is illustrated. In the method an excitation force 120 imparts a vibration force to each test mesh point 102. The spectrum analyzer 122 collects the response of all the accelerometers 110 and the excitation force 120, transforms the results into the frequency domain, and sends the results to a microcomputer 130 for further analysis in accordance with the present invention.

Figure 2:
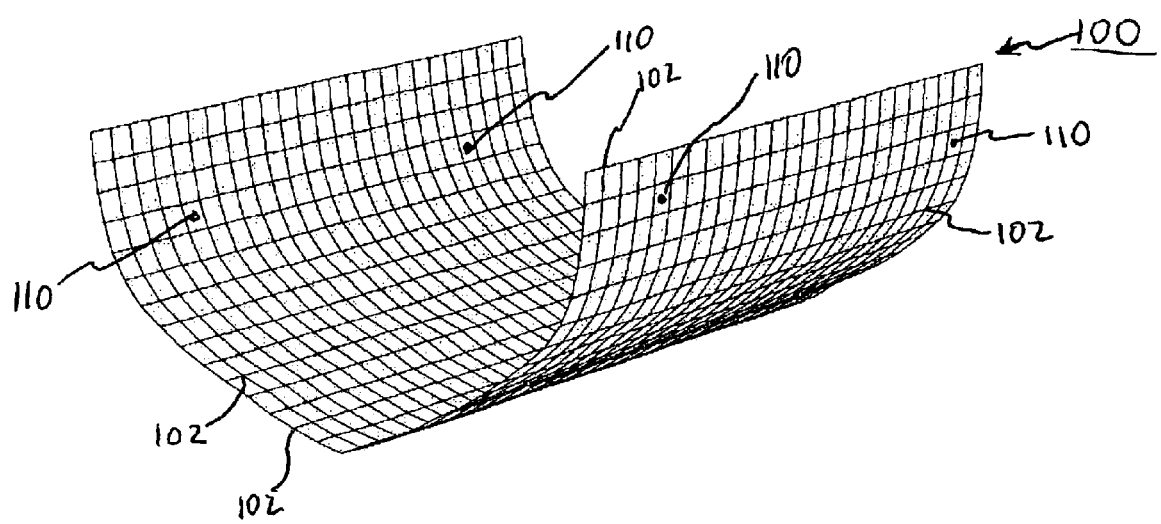
FIG. 2 is an experimental test mesh applied to a ship hull section in accordance with the present invention.

The example of FIG. 2 shows a regular mesh pattern 100 of test points 102 (all intersecting points are understood to be the same for labeling purposes) that was imposed on a composite ship hull section (not shown). The test mesh pattern 100 is comprised of intersecting lines that run latitudinal and longitudinally. Although the lines are referred to as running latitudinal and longitudinally, it is not necessary for the two directions to be orthogonal, or even in a flat plane as skewed or curved lines are equally effective. On the section of ship hull illustrated in FIG. 2, the analysis lines followed the curve of the hull cross section.

In the example of FIG. 2, sensors 110 are placed at four relatively symmetric locations. The accelerometers 110 are placed close to symmetric, but with some deliberate asymmetry, with each transducer 110 being positioned close to, but away from, extreme edges or corners of the test structure. The accelerometers 110 in the present example had a nominal sensitivity of 100 MV/g. Various types of sensors 110 may be used such as strain gages, mems sensors, fiber optic Bragg gratings, or other types of strain or displacement transducers.

Though four accelerometers 110 were used in this example, the invention does not specify a set number and can work with other numbers of accelerometers 110. Generally, using fewer sensors 110 may result in spurious damage indications. Increasing the number of sensors 110 would require additional processing and testing time, but would yield some improvement in the results obtained.

Once the test composite structure is covered with a test mesh 100 and accelerometers 110 then the structure is impulsively force excited with an instrumented exciter 120 as illustrated in FIG. 1 at each test point 102 twice. The exciter 120 must be capable of imparting sufficient vibrational energy in the frequency range of interest. In a preferred embodiment, the frequency range is from zero to approximately one hundred times the fundamental frequency of the structure. In the example, a modally tuned 2 lb sledge with a built-in force transducer was used as the prime excitation force 120.

Figure 3:
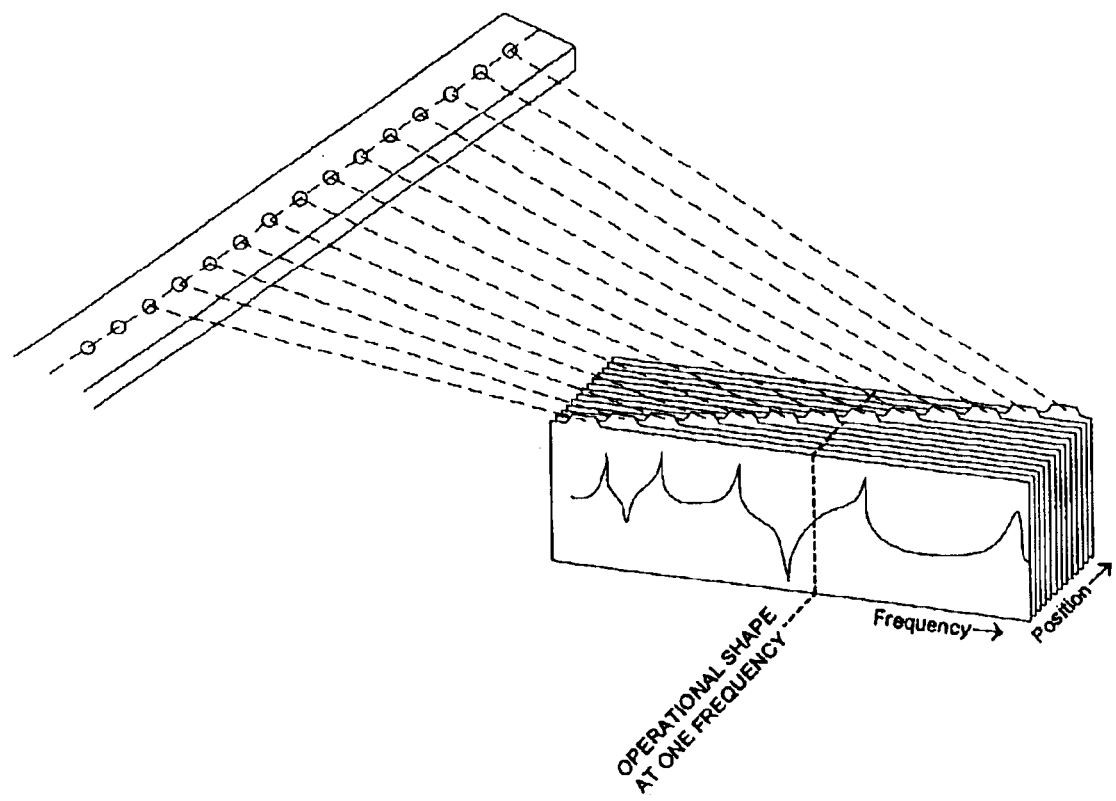
FIG. 3 is a graphical view of the Frequency Response Functions (FRF) for an array of test points.

Each single excitation and all the response signals, in the form of acceleration, are measured at a fixed location by each accelerometer 110 and are captured on a signal or spectrum analyzer 122. As illustrated in FIG. 3, Frequency Response Functions (FRF) are then determined by transforming the temporal force and acceleration data to the frequency domain using Fast Fourier Transforms (FFTs). With this frequency information at each location the displacement shape at any chosen frequency is known. The Fourier analysis gives the response at each frequency as if the structure had been excited with a sine wave at that frequency. For example, in FIG. 2, a FRF is measured between each interrogation point 102 on the structure and the fixed accelerometers 110. The FRF at each interrogation point 102 is the frequency average of each of the two responses recorded.

Figure 4A:
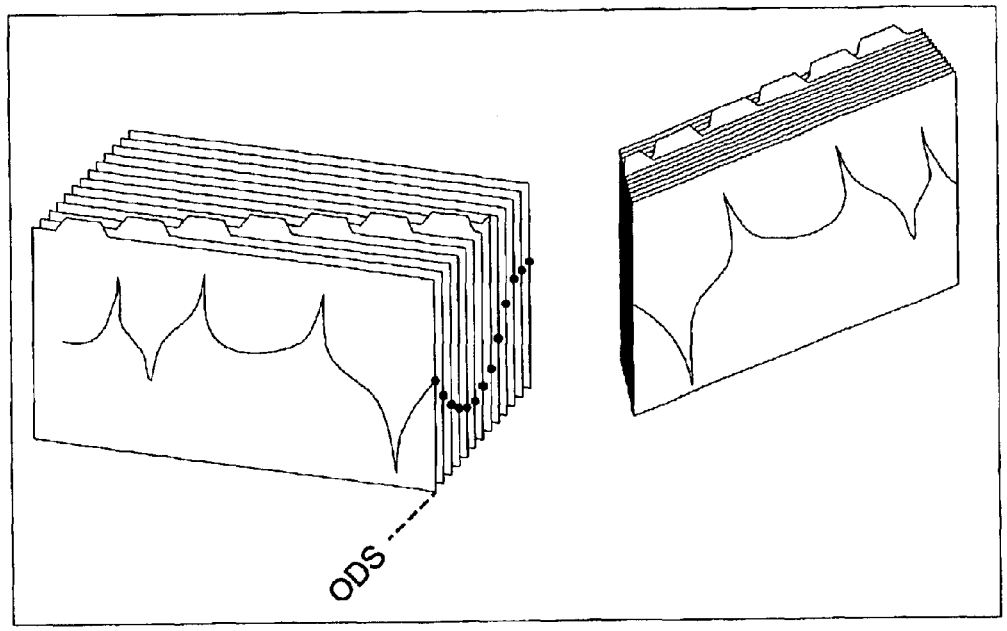
FIG. 4A is a graphical view illustrating the array of values of the Frequency Response Functions (FRF) at a chosen frequency representing the Operation Deflection Shape (ODS).
Figure 4B:
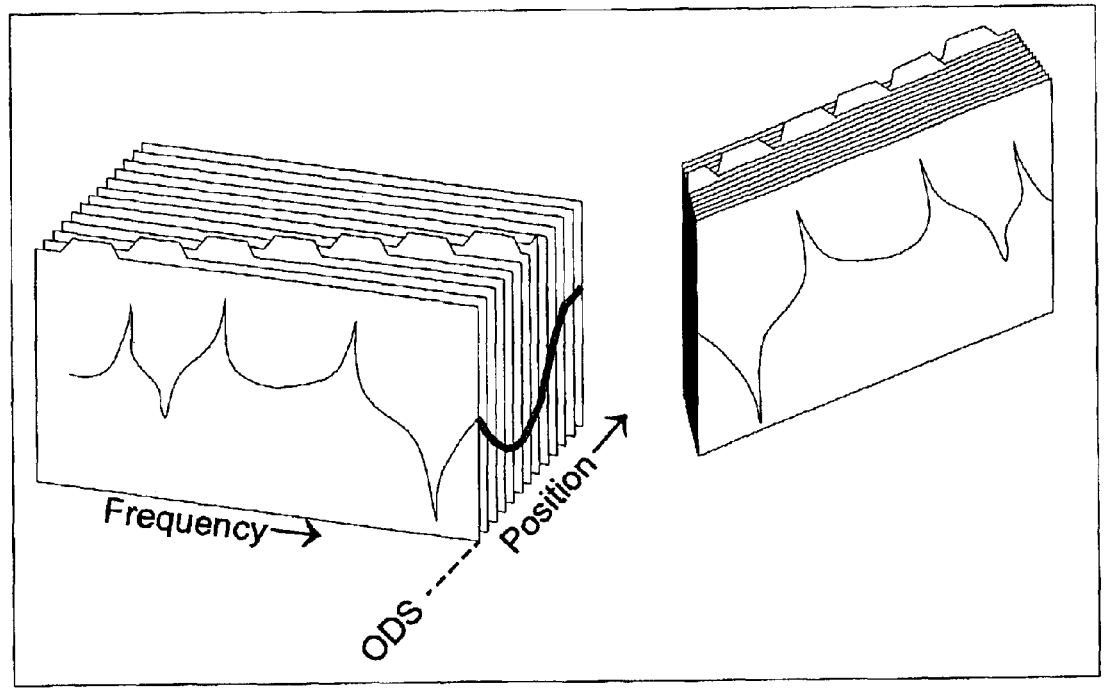
FIG. 4B is a graphical view illustrating a curve fitted to the array of values of the Frequency Response Functions at a chosen frequency.

As shown in FIG. 4A the Operation Deflection Shape (ODS) is the array of values of the FRFs at a chosen frequency. FIG. 4B shows the ODS constructed using the FRF versus position information with a curve drawn to connect the discrete points. This gives the ODS as a function of position for the entire structure at each of the interrogation points 102.

Once the ODS for each analysis frequency has been determined, it is spatially differentiated to convert it to an Operating Curvature Shape (OCS) using the finite difference approximations of equation (1) below, which are applied separately to the real and imaginary parts of the ODS.

In equation (1) $y_i$ is the value of the ODS at the i-th spatial position on the structure, and h is the spatial separation between test points. $C_i$ is the resulting value of the OCS for the i-th spatial position. The curvatures for the first and last points are calculated using a four-point backward/forward looking finite difference approximation, while the other curvatures are calculated using a three-point central difference approximation. All approximation equations have an accuracy indicated by the Bachmann-Landau order of magnitude, $O(h^2)$. Note that when the measured FRFs are acceleration-based, as is often the case for experimental work, the acceleration measurements do not have to be converted to displacement.

$$C_i=(y_{i+1}-2y_i+y_{i-1})/h^2 \text{ for the i-th general point } C_1=(2y_1-5y_2+4y_3-y_4)/h^2 \text{ for the 1 st point } C_N=(2y_N-5y_{N-1}+4y_{N-2}-y_{N-3})/h^2 \text{ for the N-th (last) point} \quad (1)$$

The OCS has a characteristic feature near a point of structural stiffness irregularity or anomaly. In order to extract this feature from the OCS, while also offering a degree of smoothing for experimental data the method is applied to a two-dimensional mesh or grid. The two-dimensional mesh enables the method to be applicable to the testing of many real structures such as the ship hull in FIG. 2, bridges, or structural beams.

The procedure (including frequency averaging) is first applied along all latitudinal lines. This results in a matrix of structural irregularity index values, one for each test point on the mesh. The procedure is then applied to all longitudinal lines, and a second matrix of structural irregularity indices is generated. The result for each direction gives an indication of the stiffness variability in that direction.

For example, a stiffener or beam running across an otherwise uniform plate will be detected by analysis lines that run across the line of the stiffener, but not by lines that run parallel to the stiffener. While the two 'directional' results can be combined to generate a summary, maintaining the result as two separate directional results can provide more useful information about the many engineering features of a structure that have a geometry that makes them amenable to this bi-directional analysis.

To apply the procedure, first a gapped cubic polynomial is fit to the OCS function, with separate functions being fitted to the real and imaginary part of the complex function. For example, the cubic calculated for the i-th element of the curvature, $C_1$, at position $x_i$, is defined by the formula $$p_0+p_1x_i+p_2x_i^2+p_3x_i^3 \quad (2)$$

where the polynomial coefficients $p_0$, $p_1$, $p_2$ and $p_3$ are determined explicitly from curvature elements $C_{i-2}$, $C_{i-1}$, $C_{i+1}$ and $C_{i+2}$. Curvature element $C_i$ is gapped from, meaning left out of, the curve fitting calculation. Edge effects are accounted for by gapping a different point from the end set of 5 curvature points. Separate cubic polynomials are determined for the real and imaginary parts of the OCS.

The structural irregularity index, $\delta_{f,j}$ for the f-th frequency and the j-th grid point is calculated as the difference between the experimental curvature and the values of the cubic polynomials calculated at that position as follows:

$$\delta_{f,j} = (p_0 + p_1 x_i + p_2 x_i^2 + p_3 x_i^3 - C_i)^2_{f, \text{REAL}} + (p_0 + p_1 x_i + p_2 x_i^2 + p_3 x_i^3 - C_i)^2_{f, \text{IMAGINARY}} \quad (3)$$

The procedure is repeated for each test point 102 on the structure. Like the ODS and OCS, the structural irregularity indices have a large dynamic range. In order to enhance the off-resonant values, each line of structural irregularity indices is normalized so that the rms value is one. The entire procedure is repeated for each frequency in the FRF. The resulting structural irregularity indices can be shown on a contour plot of frequency versus position. In order to generate a graphical result that is easier to interpret, the structural irregularity indices for each spatial point 102 can be frequency-averaged. This is accomplished by summing the structural irregularity index values across all frequencies at each location and then plotting the results on a contour map of the structural irregularity index values at each of the array locations 102.

The severity of damage detected in different parts of a structure is ranked using a normalization procedure. One of the major benefits of the procedure is in using both the on- and off-resonant data. This approach significantly increased the sensitivity when compared to using just resonant (or modal) data. However, broadband vibration data typically have a very large dynamic range. In order to have the results for every frequency carry comparable weight, the procedure includes normalization such that the rms structural irregularity index at each frequency is one. For example, considering a real, multi-dimensional structure covered with test mesh 100 as illustrated in FIG. 2. It is to be expected that some analysis lines will traverse parts of the structure where there is no significant stiffness variation or localized damage; other lines may traverse regions that have structural features which provide significant stiffness variations or where multiple damage locations exist. Consequently, when the damage indices along each analysis line are normalized, the rms=1 results from lines without regions of stiffness variability or damage, are comparable in magnitude to the rms=1 results from analysis lines with one or more regions of structural variability or localized damage sites. This can degrade the method's ability to identify and locate regions where stiffness variations occur in multiple locations.

In order to overcome this problem the normalization procedure is modified to normalize the ODS at each frequency such that the ODS has an rms=1 value before it is converted to curvature. This approach is based on the well known fact that damage causes very little change to deflection shapes. The procedure is then applied to this new curvature shape. The resulting structural irregularity indices are not normalized. Thus, the dynamic range problem is addressed at the displacement shape calculation, rather than at the structural irregularity index calculation. The result is that when there is no damage along the analysis line, the structural irregularity indices are very small (zero if there were no measurement noise); structural irregularity indices will be higher for analysis lines crossing significant areas of damage. Since the structural irregularity index levels have comparative meaning, the different areas located by the procedure can be ranked for importance.

It should be noted that the method detects structural stiffness variability without the need for a baseline of information (either finite element or experimental) about a presumably undamaged structure. Providing the structure is reasonably homogeneous, the stiffness variability detected by the procedure can be attributed to damage. For more complex structures, the results relate to the inherent structural variability. In this case damage is detected by calculating the change in structural irregularity index values when compared to a baseline of information. Repeatability of the test results is important for such comparison data to be useful.

Figure 6:
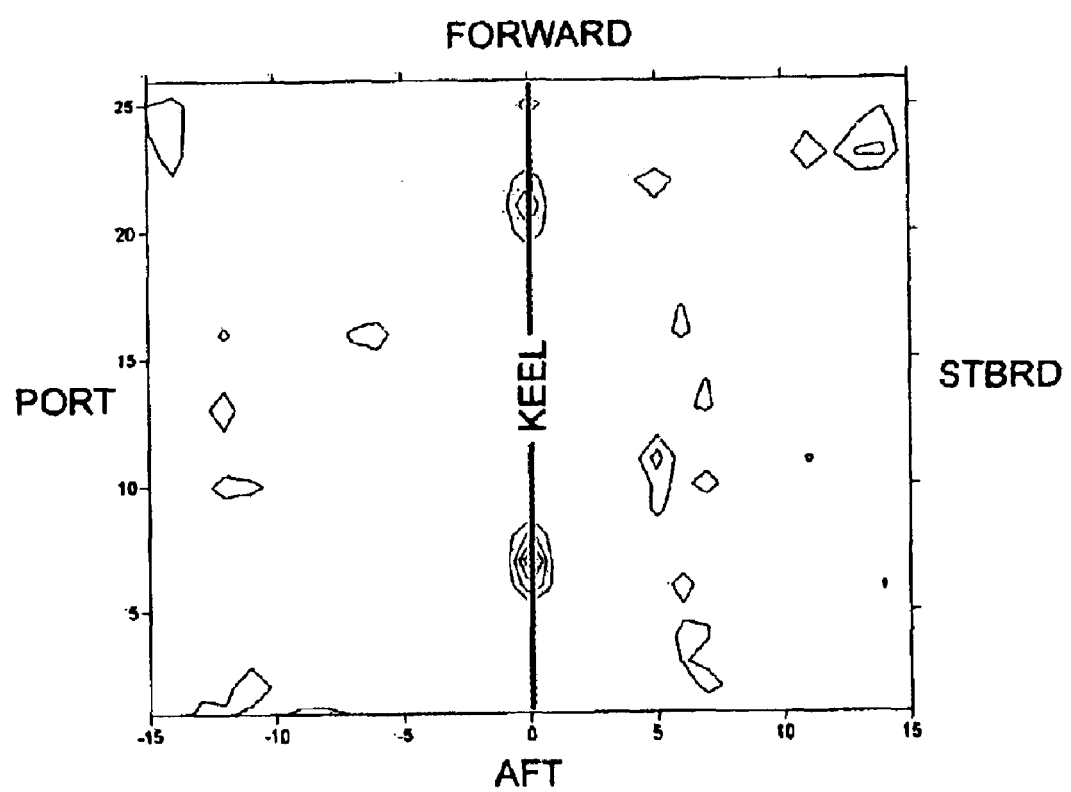
FIG. 6 is a graph depicting the differences between consecutive tests conducted in accordance with the present invention.

Repeatability is demonstrated by a repeat test of a structure when there was no damage to the structure between tests. In FIG. 6, the difference in the structural irregularity index values at each of the grid points 102 was determined and plotted. The calculated difference is effectively zero for all locations except one spot on the keel line that corresponds to a location on the underside of the hull that was extremely difficult to gain physical access to in the test. In addition to determining structural irregularities on a structure, the method of the present invention may also be used to determine locations in structures where changes in structural properties have occurred.

Figure 5A:
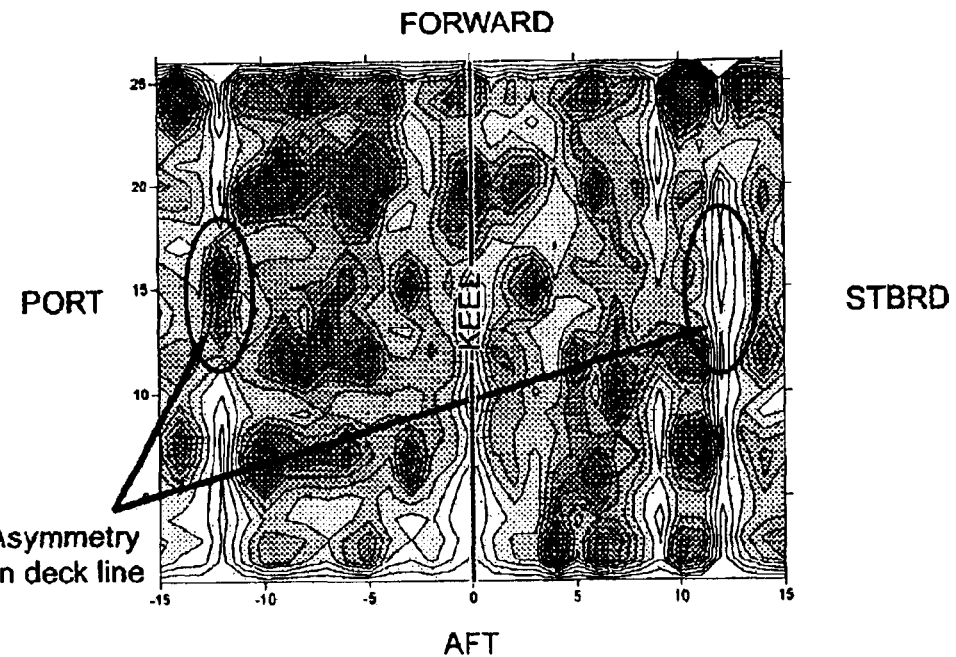
FIG. 5A is a graph of the structural irregularity and damage evaluation routine results for the fore/aft analysis lines of the ship hull.
Figure 5B:
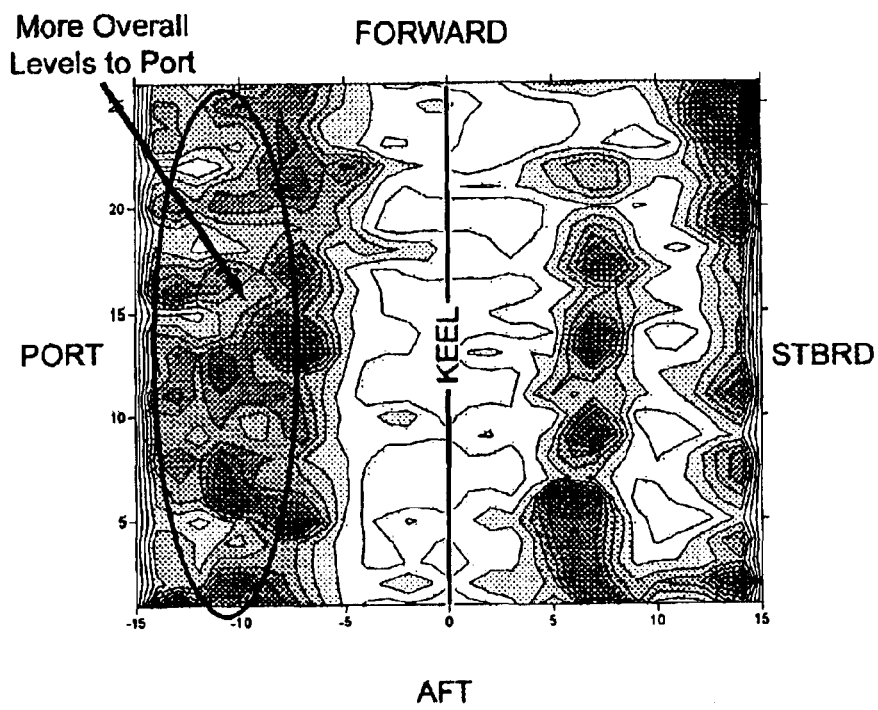
FIG. 5B is a graph of the structural irregularity and damage evaluation routine results for the port/starboard analysis lines of the ship hull.

FIGS. 5A and 5B illustrate structural irregularity index plots of a test inspection of a composite ship hull section utilizing the test mesh 100 setup as shown in FIG. 2 and applying the method of the present invention described above. FIG. 5A shows an example plot of damage indices for the structure in one direction. The method of the present invention is applied longitudinally. Applying the method in this direction enables structural irregularities that occur in the latitudinal direction to be more readily identified. FIG. 5A highlights with circles areas of difference. The contour lines on the plots are lines of identical structural irregularity index value. The larger the value, the greater the indication of a structural irregularity. FIG. 5B shows an example plot of structural irregularity indices applying the method in the latitudinal direction. This analysis will identify irregularities in the longitudinal direction. On the starboard side, there is a strong indication of the stiffener, as would be expected. On the port side, there is no strong indication of the stiffening that would be associated with a stiffener. Instead, the port side shows many areas where there are indications of irregularities that do not correspond to known structural features. This indicates that the port side has less structural integrity than the starboard side.

Figure 7:
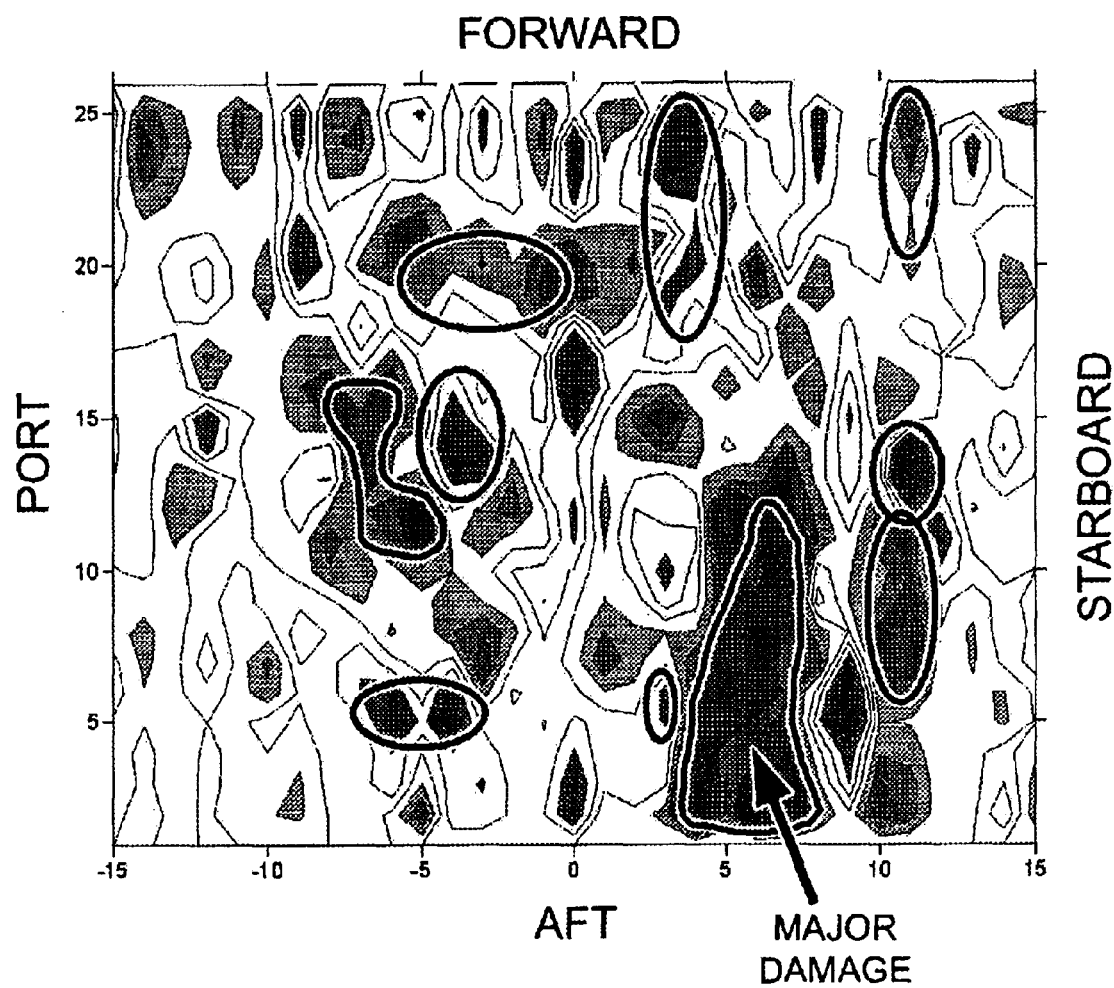
FIG. 7 is a graphical illustration of the damage assessment of the ship hull.

FIG. 7 illustrates the results of the structural irregularity index testing that was performed on the ship hull structure after it was subjected to significant loading which was purposefully large enough to cause damage to the hull structure. FIG. 7 also shows the difference between the first inspection, illustrated in FIGS. 5A and 5B, and after the hull structure was intentionally damaged. Anomalies identified using this difference, or baseline method, indicate actual damage to the structure being tested. The areas indicating damage to areas of the hull section are highlighted in FIG. 7.

It will be appreciated that many of the method steps set forth may be performed manually. However, many of the mathematical calculations and iterative steps are ideally suited to be performed by a computer system 130 under the control of operational software program code as illustrated in FIG. 3. The computer system includes a processor, random access memory, some form of mass data storage, and a user interface (none of which are shown). The computer system 130 may comprise a personal computer, workstation, or any other suitable computing or processing system.

While there have been described what are believed to be the preferred embodiments of the present invention, those skilled in the art will recognize that other and further changes and modifications may be made thereto without departing from the spirit of the invention, and it is intended to claim all such changes and modifications that fall within the true scope of the invention.

What is claimed is:

1. A nondestructive inspection method for structures comprising:

providing a plurality of test points covering the structure in a marked mesh;

providing a plurality of sensors attached to said structure;

imparting a vibration force in said structure at each said test point;

recording the input of said vibration force and said sensor response of said structure;

determining the frequency response function (FRF) from said vibration force excitation at each of said test points;

determining the frequency dependent Operating Deflection Shapes (ODS) from the FRF's at each frequency and each of said test points;

differentiating the ODS to convert the information to an Operating Curvature Shape (OCS) using the finite difference approximation applied to both the real and imaginary parts of the ODS;

fitting a gapped cubic polynomial to the OCS of the 5 nearest neighbor points of said test points with separate functions being fitted to the real and imaginary parts of the complex function where the center value of the OCS has been removed;

calculating the difference between the experimental curvature and the values of said cubic polynomials at each frequency and each said test point on said mesh, whereby this difference is called the structural irregularity index;

summing the structural irregularity index values across all frequencies at each said test point;

plotting the results on a contour map of said structural irregularity index values at each of said mesh test points.

2. The method as recited in claim 1, wherein said ODS is normalized to an rms value of 1.

3. The method as recited in claim 2, wherein said vibration force is an instrumented impulse hammer.

4. The method as recited in claim 3, wherein said force is in a frequency range of approximately one to one hundred times the fundamental frequency of said structure.

5. The method as recited in claim 3, wherein said vibration force frequency corresponds to the resonant frequencies of said structure.

6. The method as recited in claim 2, wherein said vibration force Is selectively excited in said structure in a range of frequencies imparted by a mechanical shaker.

7. The method as recited in claim 2, wherein said structure is selectively excited using a random vibration from a mechanical shaker.

8. The method recited in claim 2, wherein said fitting of the gapped cubic polynomial to the OCS is done in one direction only.

9. The method recited in claim 2, wherein said fitting of the gapped cubic polynomial to the OCS is the sum of the process done in two intersecting directions of said mesh of said test points.

10. The method as recited in claim 2, wherein said sensors are fiber optic Bragg gratings.

11. The method as recited in claim 2, wherein said sensors are mems sensors.

12. The method as recited in claim 2, wherein said sensors are strain gages.

13. The method as recited in claim 1, wherein said ODS is not normalized to an rms value of one and wherein the rms value of said damage indices at each line is normalized to an rms value of 1.

14. The method as recited in claim 13, wherein said vibration force is an instrumented impulse hammer.

15. The method as recited in claim 14, wherein said force is in a frequency range of one to one hundred times the fundamental frequency of said structure.

16. The method as recited in claim 14, wherein said vibration force frequency corresponds to the resonant frequencies of said structure.

17. The method as recited in claim 13, wherein said vibration force is selectively excited in said structure in a range of frequencies imparted by a mechanical shaker.

18. The method as recited in claim 13, wherein said structure is selectively excited using a random vibration from a mechanical shaker.

19. The method as recited in claim 13, wherein said structure is selectively excited using swept-sine vibration.

20. The method recited in claim 13, wherein said fitting of the gapped cubic polynomial to the OCS is done in one direction only.

21. The method recited in claim 13, wherein said fitting of the gapped cubic polynomial to the OCS is the sum of the process done in two intersecting directions of said mesh of said test points.

22. The method as recited in claim 13, wherein said sensors are fiber optic Bragg gratings.

23. The method as recited in claim 13, wherein said sensors are mems sensors.

24. The method as recited in claim 13, wherein said sensors are strain gages.

25. A nondestructive inspection method for structures comprising:

establishing and marking a rectangular array of points on the structure which covers the entire structure;

attaching a number of sensors to the structure, wherein said sensors are not located on the rectangular grid and are at locations that are asymmetric and at regions that are large distances from each other;

imparting vibrational energy to the structure in a frequency range that is from one to up to one hundred times the fundamental frequency of the structure;

recording the input of the impulse hammer and sensor response of the structure to a microcomputer;

determining the average frequency response function (FRF) from two impulse excitations at each of the locations marked of the rectangular array of points;

determining the frequency dependent Operating Deflection Shapes (ODS) from the FRF's at each frequency and each point of the rectangular array;

normalizing the deflection to an rms value of 1;

differentiating the ODS to convert the information to an Operating Curvature Shape (OCS) using the finite difference approximation applied to both the real and imaginary parts of the ODS;

fitting a gapped cubic polynomial to the OCS of 5 nearest neighbor locations of the rectangular array of points with separate functions being fitted to the real and imaginary parts of the complex function where the center value of the OCS has been removed;

calculating the difference between the experimental curvature and the values of the cubic polynomials at each frequency and each location on the retangular array where this difference is called the structural irregularity index;

summing the structural irregularity index values across all frequencies of interest at each location;

plotting the results on a contour map of the structural irregularity index values at each of the rectangular array locations.

26. The method as recited in claim 25, wherein said vibration force is an instrumented impulse hammer.

27. The method as recited in claim 26, wherein said force is in a frequency range of one to approximately one hundred times the fundamental frequency of said structure.

28. The method as recited in claim 26, wherein said vibration force frequency corresponds to the resonant frequencies of said structure.

29. The method as recited in claim 25, wherein said vibration force is selectively excited in said structure in a range of frequencies imparted by a mechanical shaker.

30. The method as recited in claim 25, wherein said structure is selectively excited using a random vibration from a mechanical shaker.

31. The method as recited in claim 25, wherein said structure is selectively excited using swept-sine vibration.

32. The method recited in claim 25, wherein said fitting of the gapped cubic polynomial to the OCS is done in one direction only.

33. The method recited in claim 25, wherein said fitting of the gapped cubic polynomial to the OCS is the sum of the process done in two mutually orthogonal directions of said rectangular array.

34. The method as recited in claim 25, wherein said sensors are fiber optic Bragg gratings.

35. The method as recited in claim 25, wherein said sensors are mems sensors.

36. The method as recited in claim 25, wherein said sensors are strain gages.

37. The method as recited in claim 25, wherein said operating deflection shape is not normalized to an rms value of one and wherein the rms value of said damage indices at each line is normalized to an rms value of 1.

38. A nondestructive inspection method for composite structures comprising:

establishing and marking a grid of points covering the composite structure;

providing a plurality of sensors attached to said structure;

imparting a vibration force to said structure;

recording the input of said vibration force and said sensor response of said structure;

determining the average frequency response function (FRF) from two impulse excitations at each of said marked grid of points;

determining the-frequency dependent Operating Deflection Shapes (ODS) from the FRF's at each frequency and each of said grid points;

normalizing the ODS to an rms value of 1;

differentiating the ODS to convert the information to an Operating Curvature Shape (OCS) using the finite difference approximation applied to both the real and imaginary parts of the ODS;

fitting a gapped cubic polynomial to the OCS of the 5 nearest neighbor points of said grid of points with separate functions being fitted to the real and imaginary parts of the complex function where the center value of the OCS has been removed;

calculating the difference between-the experimental curvature and the values of said cubic polynomials at each frequency and each point on said grid, whereby this difference is called the structural irregularity index;

summing the structural irregularity index values across all frequencies at each said point;

plotting the results on a contour map of said structural irregularity index values at each of said grid points.

* * * * *